United States Patent [19]

Grosskinsky et al.

[11] Patent Number: 4,629,613

[45] Date of Patent: Dec. 16, 1986

[54] STABILIZED SOLUTIONS OF HYDROXYLAMINE OR ITS SALTS IN WATER OR ALCOHOLS, AND THEIR PREPARATION

[75] Inventors: Otto-Alfred Grosskinsky; Elmar Frommer; Josef Ritz, all of Ludwigshafen; Erwin Thomas, Freinsheim; Franz-Josef Weiss, Neuhofen, all of Fed. Rep. of Germany

[73] Assignee: BASF Aktiengesellschaft, Ludwigshafen, Fed. Rep. of Germany

[21] Appl. No.: 682,071

[22] Filed: Dec. 17, 1984

[30] Foreign Application Priority Data

Dec. 17, 1983 [DE] Fed. Rep. of Germany ....... 3345734

[51] Int. Cl.$^4$ ............................................. C01B 21/20
[52] U.S. Cl. .................................... 423/265; 423/387; 260/501.17; 546/153; 546/179; 252/188.28; 252/403
[58] Field of Search ............................ 252/403, 188.28; 260/501.17; 423/265, 387; 546/153, 179

[56] References Cited

U.S. PATENT DOCUMENTS

| | | | |
|---|---|---|---|
| 3,113,135 | 12/1963 | Hodel | 546/179 X |
| 3,145,082 | 8/1964 | Rausch et al. | 423/275 |
| 3,480,391 | 11/1969 | Carlos | 423/387 |
| 3,480,392 | 11/1969 | Carlos | 423/387 |
| 3,544,270 | 12/1970 | Carlos | 423/265 |

FOREIGN PATENT DOCUMENTS

| | | | |
|---|---|---|---|
| 100908 | 6/1982 | Japan | 423/387 |
| 69844 | 4/1983 | Japan | 423/387 |

OTHER PUBLICATIONS

Kawashima, et al., "Antioxidative and Quantum Chemical Properties of Some Hydroxy N-Heterocyclic Compounds", J. Agric. Food Chem., vol. 27, No. 6, (1979), pp. 1409-1410.

Primary Examiner—John F. Terapane
Assistant Examiner—Matthew A. Thexton
Attorney, Agent, or Firm—Keil & Weinkauf

[57] ABSTRACT

Stabilized solutions of hydroxylamine or its salts in water or alcohols, containing 8-hydroxyquinaldines, and their preparation.

4 Claims, No Drawings

STABILIZED SOLUTIONS OF HYDROXYLAMINE OR ITS SALTS IN WATER OR ALCOHOLS, AND THEIR PREPARATION

Solutions of hydroxylammonium salts decompose slowly at room temperature and more rapidly at elevated temperatures, this behavior being more pronounced in the case of solutions of free hydroxylamine. There has been no lack of attempts to stabilize solutions of hydroxylamine and its salts in order to achieve a longer shelf life. For example, according to U.S. Pat. No. 3,544,270, urea derivatives are used as stabilizers, and U.S. Pat. No. 3,480,391 discloses that amidoximes are suitable stabilizers. According to U.S. Pat. No. 3,480,392, hydroxamic acids can be used for this purpose. Furthermore, U.S. Pat. No. 3,145,082 discloses the use of chelate-forming agents, such as sodium ethylenediaminetetraacetate, as stabilizers, and Japanese Pat. No. 82, 100,908 discloses that 8-hydroxyquinoline is a suitable stabilizer for hydroxylamine. The stabilizers used to date are unsatisfactory.

It is an object of the present invention to provide stabilized solutions of hydroxylamine or its salts which are stable over a prolonged period and in which, in particular, the decomposition of free hydroxylamine is minimized, even at slightly elevated temperatures.

We have found that this object is achieved by stabilized solutions of hydroxylamine or its salts in water or alcohols, which contain 8-hydroxyquinaldines.

The present invention furthermore relates to a process for the preparation of stabilized solutions of hydroxylamine or its salts by the addition of stabilizers, wherein the molecular oxygen dissolved in the solution to be stabilized is removed from this solution by treatment with nitrogen which is free of molecular oxygen, and 8-hydroxyquinaldines are then added.

The solutions of hydroxylamine or its salts which have been stabilized according to the invention have the advantage that they are stable over a longer period than prior art solutions, and in particular the decomposition of free hydroxylamine is reduced to a minimum even at slightly elevated temperatures.

According to the invention, a solution of hydroxylamine or one of its salts in water or an alcohol, eg. a $C_1$–$C_4$-alkanol, is used as the starting material. Examples of suitable salts of hydroxylamine are those with a strong mineral acid, such as sulfuric acid, nitric acid or hydrochloric acid, or those with fatty acids, eg. acetic acid or propionic acid. Because of the difference in solubilities, hydroxylamine is preferably in the form of a solution in water or an alcohol, whereas its salts are preferably present as aqueous solutions. The content of hydroxylamine or its salts is, as a rule, from 10 to 70% by weight. Particularly preferably, aqueous solutions of hydroxylamine are used as starting materials, these solutions generally having a pH of from 8 to 11.

The stabilizers used are 8-hydroxyquinaldines, preferred compounds being those of the formula

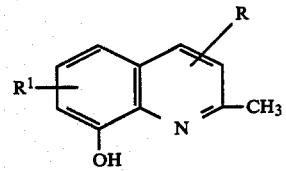

I where R and $R^1$ are each hydrogen, hydroxyl, $C_1$–$C_4$-alkoxy or $C_1$–$C_4$-alkyl. Examples of suitable 8-hydroxyquinaldines are 6-methyl-8-hydroxyquinaldine and 5,8-dihydroxyquinaldine, 8-hydroxyquinaldine being particularly preferred.

Advantageously, quinaldines of the formula I are used in amounts of from 0.005 to 1, in particular from 0.01 to 0.1, % by weight, based on the solution to be stabilized. The presence of polyhydroxybenzenes, in particular pyrogallol, in addition has also proven useful, the polyhydroxybenzenes advantageously being added in amounts of from 0.005 to 0.1% by weight, based on the solution to be stabilized. It is noteworthy that the combined use of 8-hydroxyquinaldines and polyhydroxybenzenes results in a synergistic effect.

Stabilized solutions of hydroxylamine or its salts in water or in alcohols are prepared, according to the invention, by a method in which the molecular oxygen dissolved in the solution to be stabilized is first displaced from this solution by treatment with nitrogen which is free of molecular oxygen so as to provide an oxygen-free stabilized solution of hydroxylamine or its salts. This is achieved by, for example, passing oxygen-free nitrogen through the solution to be stabilized, for example for from 5 to 10 minutes. The nitrogen used advantageously contains less than 2 ppm of oxygen. 8-hydroxyquinaldines and, if required, polyhydroxybenzenes are then added, and are dissolved in the said solution, the temperature advantageously being kept at from 5° to 40° C. during this procedure. It is also possible to add the stabilizers in the form of solutions, eg. in a $C_1$–$C_4$-alkanol, to the solution to be stabilized.

It is advantageous if the solution to be stabilized is prevented from becoming contaminated with heavy metals, in particular copper or noble metals, since these catalyze the decomposition of hydroxylamine. It has proven useful for the content of heavy metals to be below 1 ppm. It is also advantageous to exclude high-energy radiation by means of suitably colored glass containers, and to store the stabilized solutions at below 40° C., for example at from 5° to 20° C.

Stabilized solutions of hydroxylamine or its salts are useful for the preparation of oximes.

The Example which follows illustrates the subject of the invention.

EXAMPLE

Oxygen-free nitrogen is passed through an aqueous solution of hydroxylamine at 20° C. for 10 minutes, after which the stabilizer is added. The concentration of hydroxylamine, the type and amount of stabilizer added and the results achieved as a function of time are shown in the Table below.

TABLE

| Stabilizer | °C. | | | | |
|---|---|---|---|---|---|
| 50 ppm of 8-hydroxyquinaldine | 5 | 0 111.90 | 743 111.80 | 1198 111.71 | hours g/l $NH_2OH$ |
| 50 ppm of 8-hydroxyquinaldine | 20 | 0 111.38 | 404 111.21 | 1195 111.05 | hours g/l $NH_2OH$ |
| 50 ppm of 8-hydroxyquinaldine | 40 | 0 111.51 | 359 110.62 | 1194 109.57 | hours g/l $NH_2OH$ |

We claim:

1. An oxygen-free stabilized solution of hydroxylamine or its salts in water or an alcohol which is stable over a prolonged period which contains an 8-hydroxyquinaldine of the formula I

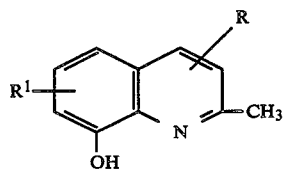

where R and $R^1$ are each hydrogen, hydroxyl, $C_1$–$C_4$-alkoxy or $C_1$–$C_4$-alkyl.

2. A stabilized solution as claimed in claim 1, which additionally contains pyrogallol.

3. A stabilized solution as claimed in claim 1, which contains from 0.005 to 1% by weight, based on the solution to be stabilized, of a quinaldine of the formula I

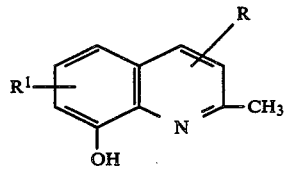

where R and $R^1$ are each hydrogen, hydroxyl, $C_1$–$C_4$-alkoxy or $C_1$–$C_4$-alkyl.

4. A stabilized solution as claimed in claim 1, wherein the starting solution used is an aqueous solution containing from 10 to 70% by weight of hydroxylamine.

* * * * *